Figure 1:
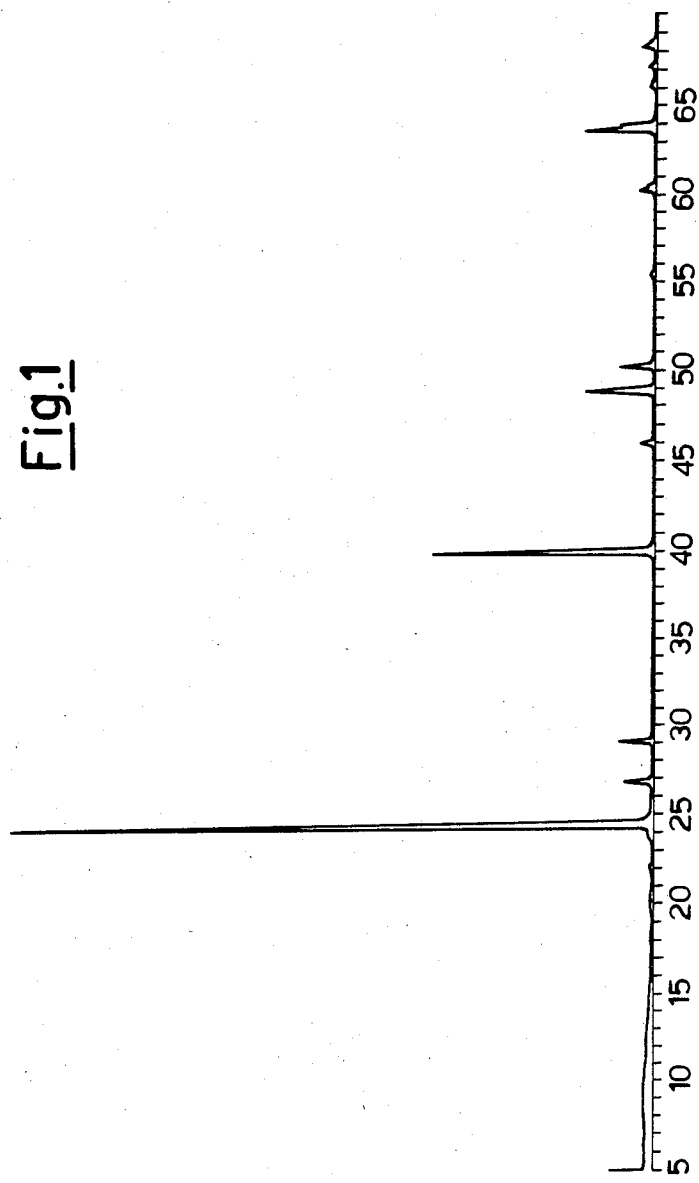

United States Patent [19]

Brunelli et al.

[11] Patent Number: 4,654,446
[45] Date of Patent: Mar. 31, 1987

[54] PROCESS FOR THE PREPARATION OF ALKYLARYLETHERS

[75] Inventors: Maurizio Brunelli, Milan; Pierferdinando Ferrari, Segrate; Fabrizio Stroppa, San Giuliano Milanese; Giuseppe Bellussi, Piacenza, all of Italy

[73] Assignee: Eniricerche S.p.A., Milan, Italy

[21] Appl. No.: 833,197

[22] Filed: Feb. 27, 1986

[30] Foreign Application Priority Data

Mar. 1, 1985 [IT] Italy ............................. 19734 A/85

[51] Int. Cl.$^4$ ............................................. C07C 41/09
[52] U.S. Cl. ................................... 568/630; 568/632; 568/648; 568/656

[58] Field of Search ................ 568/630, 632, 648, 656

[56] References Cited

U.S. PATENT DOCUMENTS 2,487,892 11/1949 Searle ................................... 568/630
4,450,306  5/1984 Eskinazi .............................. 568/630
4,487,976 12/1984 Farasiv ................................ 568/630
4,533,758  8/1985 Wells et al. ......................... 568/630

Primary Examiner—Bernard Helfin
Attorney, Agent, or Firm—Birch, Stewart, Kolasch and Birch

[57] ABSTRACT

Alkylarylethers are produced according to the invention using phenols and ethers of aliphatic alcohols as the starting materials, in the presence of $BPO_4$.

2 Claims, 1 Drawing Figure

PROCESS FOR THE PREPARATION OF ALKYLARYLETHERS

The present invention relates to a process for the preparation of alkylarylethers.

More particularly, the present invention relates to a process for the preparation of alkylarylethers using phenols and ethers of aliphatic alcohols as the starting materials.

The preparation of arylalkylethers starting from phenols and from ethers of aliphatic alcohols in the presence of strongly acidic ion-exchange resins is known (see European Pat. No. 13924).

The use of ion-exchange resins has however the drawback that operating at high temperatures over long time periods is not possible, in that under such conditions, such resins tend to loose their physical and mechanical characteristics.

As a result, operating at low temperature with consequent strong reduction in yields is necessary, or, when operating at high temperature, frequently replacing the resin is necessary.

It has been surprisingly found, and this is the object of the present invention, that replacing crystalline boron phosphate to the strongly acidic resins of the known art is possible.

The process according to the present invention comprises the steps of contacting a phenol or a mixture of phenols with an ether of aliphatic alcohols or a mixture of ethers of aliphatic alcohols, at a temperature comprised within the range of from 150° to 400° C., preferably of from 200° to 300° C., in the presence of crystalline boron phosphate, and of separating the alkylarylether obtained from the other reaction components by fractionation or crystallization.

The boron phosphate shall be defined in its characteristics in Example 1, as well as a method for its preparation shall be given, which is not to be intended as being limitative of the invention.

The reaction between the phenol, or mixture of phenols, and the ether of aliphatic alcohols, or the mixture of ethers of aliphatic alcohols can take place in the presence of a solvent, or in the absence thereof.

As solvents, when used, hydrocarbons, of preferably aromatic nature, in particular, toluene, are used.

Boron phosphate is used in amounts by weight comprised within the range of from 0.5% to 50% relatively to the weight of the reactants.

The process is carried out under atmospheric pressure, or under a greater than atmospheric pressure.

The process can be carried out batchwise or continuously.

In case of continuous operation, the catalyst is placed in a fixed or fluid bed, and the reactants are fed continuously over it, while the reaction products are continuously drawn from the side opposite to the reactant introduction side.

In case of batchwise operation, at end of reaction the catalyst is removed by filtering or centrifuging before the separation of alkylaryl ether.

The phenols can be selected among: phenol, phenols substituted with $C_1$-$C_4$ alkyl groups, such as meta-, ortho-, para-cresol, xylenols and tert.butyl-phenol, phenols substituted with halogen atoms (e.g., ortho-, meta-, para-chloro-phenol), polyphenols such as hydroquinone and pyrocatechol, alpha- and beta-naphthol, and hydroxyanthracene.

The ethers are selected among the ethers of aliphatic alcohols with a number of carbon atoms comprised within the range of from 1 to 8, preferably from 1 to 4, in particular among dimethylether, diethylether, dipropylether, diisopropylether, diisobutylether, di-tert.butylether.

The following Examples are now supplied to the purpose of better illustrating the invention, it being intended that the invention is not to be considered as being limited to them or by them.

EXAMPLE NO. 1

In a beaker of pyrex glass 1000 g of distilled water are heated at 70° C., and to them 92.7 g of $H_3BO_3$ are added under stirring. When all boric acid has been dissolved, always under stirring, 172.8 g of $H_3PO_4$ (aqueous solution at 85%) is added.

Stirring is continued, while evaporating off water, until a slurry is obtained.

The solid is dried at 100° C., it is then calcined at 1000° C. for two hours. The calx is then washed 4 times, each time redispersing it in a liter of boiling distilled water, and filtering it off. The solid obtained after drying is submitted to analysis by powder X-ray diffraction. The spectrum obtained is shown in FIG. 1, and it shows the product to be crystalline boron phosphate in the characteristic tetragonal form having the parameters:

a=4.339 (2) A
c=6.641 (3) A.

In FIG. 1 in abscissa angle $2\theta$ (Cu K$\alpha$=1,5418 A) and in ordinate the relevant intensity is reported.

EXAMPLE NO. 2

In a 200-ml autoclave of stainless steel, provided with magnetic stirrer, 22.04 parts of $BPO_4$ prepared as described in Example N. 1, and 50.55 parts of a mixture constituted by phenol (24% by weight), dimethylether (DME) (18.99% by weight), toluene (57.01% by weight) and water (0.06% by weight referred to overall weight) were charged.

The reactants were kept 48 hours at the temperature of 280° C. and under a pressure of 40 atm.

The gas-chromatographic analysis of obtained products gave the following result: DME (14.80% by weight); methanol (1.17% by weight); toluene (57.01% by weight); anisole (14.69% by weight); methylanisole (0.45% by weight); phenol (10.62% by weight); cresol (0.20% by weight); $H_2O$ (1.06% by weight).

The yield in anisole has been of 53% by mol, and the selectivity of 96% by mol.

EXAMPLE 3

In the same autoclave, and with the same modalities as in the foregoing Example, 22.41 parts of $BPO_4$ and 55.95 parts of a mixture constituted by toluene (55.67% by weight), phenol (23.37% by weight), dimethylether (DME) (20.90% by weight), and water (0.06% by weight) were charged at the temperature of 220° C. and under a pressure of 25 bar.

The gas-chromatographic analysis of the products gave the following result: DME (19.73% by weight); methanol (0.60% by weight); toluene (55.35% by weight); anisole (2.83% by weight); phenol (20.80% by weight); water (0.69% by weight).

The yield in anisole has been of 11% and the selectivity of about 100%.

We claim:

1. Process for the preparation of alkylarylethers using a phenol or a mixture of phenols and an ether of aliphatic alcohol or a mixture of ethers of aliphatic alcohols as the starting products, characterized in that the catalytic system is $BPO_4$, the reaction temperature being selected within the range of from 150° to 400° C.

2. Process according to claim 1, characterized in that the temperature is selected within the range of from 200° to 300° C.

* * * * *